United States Patent [19]

Forné et al.

[11] Patent Number: 4,535,159

[45] Date of Patent: Aug. 13, 1985

[54] PROCESS FOR PRODUCING 1-POSITION AMINO-DERIVATIVES OF 1-(3′,4′-METHYLENEDIOXYPHENYL)PROPANE-2-OL

[75] Inventors: Ernesto Forné ; Rafael Foguet; Aurelio Sacristán; José A. Ortiz, all of Barcelona, Spain

[73] Assignee: Ferrer Internacional, S.A., Barcelona, Spain

[21] Appl. No.: 374,593

[22] Filed: Apr. 30, 1982

[30] Foreign Application Priority Data

May 13, 1981 [ES] Spain ..................................... 502.470

[51] Int. Cl.³ .................. C07D 413/00; C07D 403/00; C07D 317/44
[52] U.S. Cl. .................... 544/148; 544/359; 546/197; 548/526; 549/443
[58] Field of Search ................ 549/435, 443; 424/282; 544/148, 359; 546/197; 548/526

[56] References Cited

U.S. PATENT DOCUMENTS

| | | | |
|---|---|---|---|
| 2,088,941 | 8/1937 | Bockmühl et al. | 549/443 |
| 2,578,696 | 12/1951 | Gump et al. | 549/443 |
| 2,765,307 | 10/1956 | Schmidle | 549/443 |
| 3,657,244 | 4/1972 | Mentrup et al. | 549/362 |
| 3,915,969 | 10/1975 | Manghisi et al. | 549/443 |

FOREIGN PATENT DOCUMENTS 2101587  1/1983  United Kingdom ................ 549/443

OTHER PUBLICATIONS

Chemical Abstracts, 98: 53375f, (1983).

*Primary Examiner*—Ethel G. Love
*Attorney, Agent, or Firm*—Michael J. Striker

[57] ABSTRACT

The present invention relates to a process for producing novel 1-position amino-derivatives of 1-(3′,4′-methylenedioxyphenyl)propane-2-ol having general formula I:

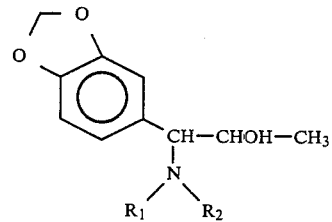

where $R_1$ and $R_2$ are hydrogen, alkyl having 1 to 2 carbon atoms, cycloalkyl having 3 to 6 carbon atoms, or benzyl, with the proviso that $R_1$ and $R_2$ are not at the same time hydrogen, cycloalkyl or benzyl and where, $R_1$ and $R_2$ taken together with the nitrogen atom to which they are attached form a ring having 5 to 7 bonds, which may contain another heteroatom selected from oxygen or nitrogen which can be substituted by benzyl or hydroxyl, as well as the non-toxic addition salts of such derivatives.

18 Claims, No Drawings

PROCESS FOR PRODUCING 1-POSITION AMINO-DERIVATIVES OF 1-(3',4'-METHYLENEDIOXYPHENYL)PROPANE-2-OL

The compounds of the present invention are obtained in accordance with the following Diagram I:

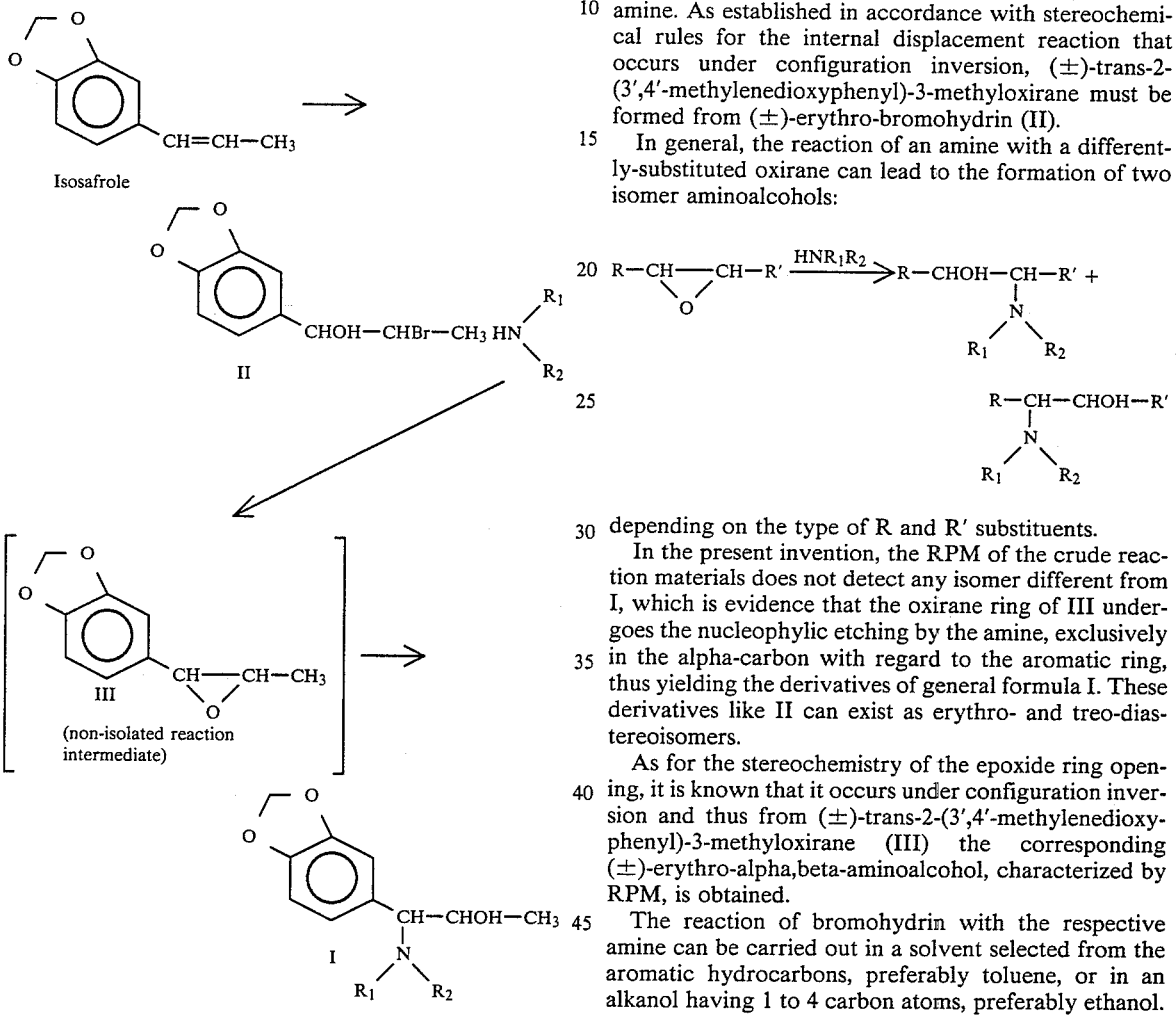

As shown above, the reaction is started using Isosafrole, a commercially-available product, having a content of E trans isomer not lower than 80% its Z cis-isomer constituting the balance.

It is a characteristic of 2-bromo-1-(3',4'-methylenedioxyphenyl)propane-1-ol (II) that it exists in the form of its erythro and treo-diastereoisomers, each having corresponding d and l optical isomers.

Synthesis of II is carried out according to the present invention by bromination of Isosafrole whether through a trans-addition of bromine to the olefin E-form to give ($\pm$)-erythro-dibromo-derivative which on solvolysis with calcium carbonate in an acetone-water mixture leads to ($\pm$)-erythro-2-bromo-1-(3',4'-methylenedioxiphenyl)propane-1-ol, which is identified in the RPM by the relatively-low value (4.0 Hz) of the proton coupling constant —CHOH— and —CHBr, or through treatment with N-bromosuccinamide and water in dimethylsulphoxide with the ($\pm$)-erythrobromohydrin also being obtained from the olefin E-form as a result of BrOH trans-addition.

The compounds of the present invention are obtained by treating the ($\pm$)-erythro-2-bromo-1-(3',4'-methylenedioxyphenyl)propane-1-ol (II) with a primary or secondary aliphatic amine having the formula $HNR_1R_2$, where $R_1$ and $R_2$ are as defined in I.

The reaction occurs through the epoxide III, which is formed in the reaction medium by basic catalysis of the amine. As established in accordance with stereochemical rules for the internal displacement reaction that occurs under configuration inversion, ($\pm$)-trans-2-(3',4'-methylenedioxyphenyl)-3-methyloxirane must be formed from ($\pm$)-erythro-bromohydrin (II).

In general, the reaction of an amine with a differently-substituted oxirane can lead to the formation of two isomer aminoalcohols:

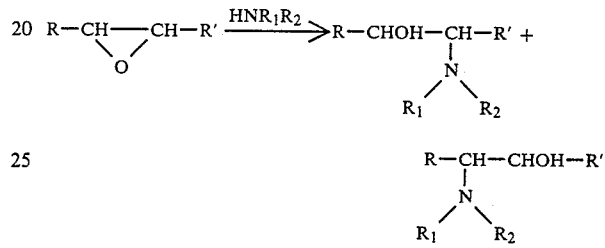

depending on the type of R and R' substituents.

In the present invention, the RPM of the crude reaction materials does not detect any isomer different from I, which is evidence that the oxirane ring of III undergoes the nucleophylic etching by the amine, exclusively in the alpha-carbon with regard to the aromatic ring, thus yielding the derivatives of general formula I. These derivatives like II can exist as erythro- and treo-diastereoisomers.

As for the stereochemistry of the epoxide ring opening, it is known that it occurs under configuration inversion and thus from ($\pm$)-trans-2-(3',4'-methylenedioxyphenyl)-3-methyloxirane (III) the corresponding ($\pm$)-erythro-alpha,beta-aminoalcohol, characterized by RPM, is obtained.

The reaction of bromohydrin with the respective amine can be carried out in a solvent selected from the aromatic hydrocarbons, preferably toluene, or in an alkanol having 1 to 4 carbon atoms, preferably ethanol.

The compounds of the present invention have analgesic activity. The pharmacological (analgesia) and toxicological evaluations of these compounds will now be described:

(a) Analgesic activity.-Analgesic activity has been determined in Swiss male mice by orally administering the compounds according to the phenylquinone test, as described by Siegmund et al (Proc. Soc.Exp.Biol.Med., 95, 729, 1957). From the analgesia values obtained, the $ED_{50}$ for each compound has been calculated. Results are shown in Table I.

(b) Acute toxicity.-Acute toxicity has been determined in both female and male Swiss mice by oral administration according to the method by Reed-Müench as modified by Pizzi (Human Biology, 22(3), 151–190, 1950). Results are shown in Table I.

The compounds of the present invention mixed with pharmaceutically acceptable carriers can be administered by the oral route in the form of tablets, capsules, syrups, solutions, etc., by the injection route and by the rectal route, in daily doses ranging from 500 to 5000 mg.

TABLE I

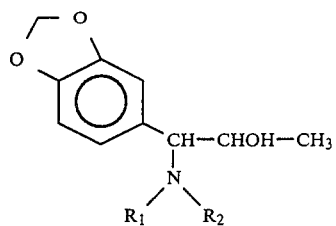

I

| $R_1$ | $R_2$ | Example | Analgesic activity $ED_{50}$ (mg/kg) | Acute toxicity $LD_{50}$ (mg/kg) |
|---|---|---|---|---|
| ⟨NO⟩.ClH | | 2 | 25.7 | 1200 |
| ⟨N−CH₂−Ph⟩.2ClH | | 3 | 29.7 | 256 |
| —CH₂CH₃ | —CH₂CH₃.ClH | 4 | 107 | 317 |
| ⟨N-cyclohexyl⟩.ClH | | 5 | 33.3 | 277 |
| ⟨N-cyclohexyl-OH⟩.ClH | | 6 | 109 | 1058 |
| ⟨N-cyclopentyl⟩.ClH | | 7 | 140.3 | 599 |
| ⟨N-cycloheptyl⟩.ClH | | 8 | 45.5 | 233 |
| —H | —CH₂—Ph.ClH | 9 | 28.8 | 252 |
| —CH₃ | —CH₂—Ph.ClH | 10 | 33.8 | 360 |
| —CH₃ | —cyclohexyl.ClH | 11 | 29.8 | 167 |
| —H | —cyclopropyl.ClH | 12 | 62.3 | 780 |
| —H | —cyclohexyl.ClH | 13 | 31.7 | 245 |
| Codeine | | | 1.97 | |
| Aminophenazone | | | 23.4 | |
| Acetylsalicylic acid | | | 72 | |

A number of examples will now be described in non-limitative manner in order to illustrate the invention. It is understood that larger quantities than those indicated can be used in industry.

EXAMPLE 1

Erythro-2-bromo-1-(3',4'-methylenedioxyphenyl)propane-1-ol (II)

(a) Using bromine, calcium carbonate and water: To a solution of 324 g of Isosafrole (2 mols) in 0.7 l of dry ethyl ether, cooled in an ice/salt bath, 324 g of bromine are added during a period of 1 hour while the reaction temperature is kept lower than 5° C.

Once the addition is completed, the ether is distilled off under vacuum, and the resulting oil, dissolved in 1.4 l of acetone is allowed to react with 324 g of water and 105.4 g of powdered calcium carbonate. The mixture is stirred under reflux in a water-bath for two hours, it is filtered with insolubilized calcium bromide and heated for a further two hours with 210 g of water. Acetone is distilled off, the residue is extracted with ethyl ether and from the organic extracts following washing and drying, 522.4 g (yield: 100%) of bromohydrin as a brown oil are obtained by evaporation of the solvent.

IR spectrum (film), cm$^{-1}$: 3540, 3440, 2980, 2900, 1505, 1490, 1445, 1245, 1200, 1095, 1045, 935, 815, 785.

RPM spectrum (CDCl$_3$), ppm% 1.56 (d, 3H, J=6.7 Hz; CH$_3$—), 2.88 (wide, 1H; —OH), 4.35 (m, 1H, J=3.8 Hz and 6.7 Hz; CHBr—), 4.88 (d, 1H, J=3.8 Hz; —CHOH—), 5.93 (s, 2H; —O—CH$_2$—O—), 6.80 and 6.90 (s, 3H; Ar—).

Using NBS in DMSO-H$_2$O: 81.05 g of Isosafrole (0.5 mols) are dissolved in 625 ml of dimethylsulfoxide, then 18 g of water are added and the mixture under stirring is cooled to 10° C. During a period of 10 minutes, 178 g of N-bromosuccinamide (1 mol) are added. After the first addition of NBS it is observed that the reaction color becomes intense while the reaction mixture spontaneously heats up to 60°-5° C. When the reaction is completed, stirring is kept up for a further 10 minutes and then the reaction mixture is poured onto a mixture of 2 l of NaHCO$_3$—H$_2$O (1:1), and cooled to 10° C. The separated oil is extracted with ethyl ether and the extracts are washed with water, dried and evaporated. The residue weighing 123.0 g (yield: 95%) appears as a resinous, brown product having the same characteristics as those obtained for the preceding product.

EXAMPLE 2 d,l-erythro-1-(3',4'-methylenedioxyphenyl)-1-morpholine-propane-2-ol (I, $R_1R_2$=—CH$_2$—CH$_2$—O—CH$_2$—CH$_2$)

A mixture of 100.0 g of bromohydrin (II) and 84.0 g of morpholine in 600 ml of anhydrous toluene is treated under reflux and stirring for 72 hours until the disappearance of starting material (TLC, silica-gel; eluent, chloroform). It is allowed to cool, the insolubilized morpholine hydrobromide (57.35 g, dry) is filtered off, and the organic solution is repeatedly extracted with 6N hydrochloric acid; the acid extracts, cooled in a water-ice bath, are brought to a highly-alkaline pH using a concentrated solution of ammonium hydroxide. The insolubilized resin formed is extracted three times with 200 ml of chloroform, the organic extracts are washed with ether, dried and concentrated to dryness. The resinous residue weighs 66.5 g.

Hydrochloride formation: To the thusly obtained base dissolved in 1 liter of dry ethyl ether and cooled in ice-bath, 30.8 ml of HCl(g) 11N ethanol solution are added. After two hours, the insolubilized hydrochloride is filtered off and dried: 69.2 g m.p., 220°-4° C. Following recrystallization in n-propanol (2.4 l) and active carbon, 30.4 g (26%) isolated the hydrochloride is having a m.p. 237.5°-238° C. (d) and elemental analysis C, H, N, Cl correct.

IR Spectrum (KBr), cm$^{-1}$: 3400, 3260, 3210, 3010, 2970, 2940, 2900-2600, 1490, 1480, 1440, 1380, 1245, 1015, 1030, 930, 880, 815.

By neutralization of the hydrochloride with ammonium hydroxide, extraction with chloroform and evaporation, the base is isolated as a white solid, m.p. 77°-8° C. (ethyl ether) and analysis is correct.

IR Spectrum (KBr), cm$^{-1}$: 3460, 2980, 2910, 2870, 2830, 1500, 1490, 1270, 1245, 1120, 1040, 1005, 920, 880.

RPM (CDCl$_3$), ppm: 0.87 (d, 3H, J=6, 7 Hz; CH$_3$—), 2.44 (2t, 4H, J=5, 3 Hz;

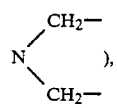

2.73 (wide, 1H; —OH), 2.96 (d, 1H, J=4 Hz; >CH—N<), 3.69 (t, 4H, J=5, 3 Hz;

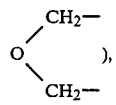

4.3 2 (m, 1H; —CHOH—), 6.00 (s, 2H; —O—CH$_2$—O—) and 6.82 and 6.96 (s, 3H; Ar—).

(b) The reaction is also carried out in ethanol, in this instance a 16-hours reflux is enough.

A similar treatment as that described in (c) above, results in the isolation of the hydrochloride under analogous yield.

EXAMPLE 3 d,l-erythro-1-(3',4'-methylenedioxyphenyl)-1-(4-benzyl-1-piperazinyl)propane-2-ol (I, $R_1R_2$=(CH$_2$CH$_2$)$_2$NCH$_2$Ph)

A mixture of 25.0 g of bromohydrin (II) and 35.80 g of 1-benzylpiperazine in 150 ml of anhydrous toluene is stirred under reflux for 72 hours, till disappearance of the starting material has taken place. Then, the mixture is cooled, the insolubilized 1-benzylpiperazine hydrochloride is filtered off (22.4 g dry), and the toluene liquors are concentrated under vacuum till dryness. The base material is separated as described in the preceding examples. There is thusly obtained a dark, viscous residue (26.0 g).

Dihydrochloride formation: the above base is dissolved in 150 ml of dry ethyl ether, and under cooling and stirring 19.6 g of 11N HCl (g) in ethanol are added. Then, after standing overnight in a refrigerator, the hydrochloride is filtered and dried thus obtaining 30.0 g of a white solid. Subsequent recrystallization in absolute ethanol and methanol-water (8:2) results in the isolation of a white pure dihidrochloride (4.6 g; 12%), having a m.p. 249°-50° C. (d). Elemental analysis of C, H, N, Cl is correct.

IR Spectrum (KBr), cm$^{-1}$: 3500, 3420, 3300, 3010, 2990, 2920, 2740-2400, 1495, 1450, 1430, 1255, 1240, 1040, 930, 920, 910, 750, 690.

Neutralization of the dihidrochloride with conc. NH$_4$OH, extraction with CHCl$_3$ and evaporation results in the isolation of the base in pure state as a viscous, transparent liquid.

IR Spectrum (CHCl$_3$), cm$^{-1}$: 3590, 3460, 3060, 2990-2700, 1610, 1485, 1440, 1370, 1350, 1280, 1130, 1100, 1005, 940, 870, 820.

RPM Spectrum (CDCl$_3$), ppm: 0.87 (d, 3H, J=6, 7 Hz; CH$_3$—), 2.41 (wide, 8H; piperazinic), 2.73 (s, 1H; —CHOH—), 2.93 (d, 1H, J=4, OHz; >CH—N<), 3.43 (s, 2H; >N—CH$_2$—Ar), 4.25 (m, 1H; —CHOH—), 5.90 (s, 2H; —O—CH$_2$—O), 6.73 and 6.84 (s, 3H; Ar—), and 7.29 (s, 5H; Ar—).

EXAMPLE 4 d,l-erythro-1-(3',4'-methylenedioxyphenyl)-1-diethylamino-propane-2-ol

I, $R_1R_2$=CH$_2$CH$_3$)

A mixture of 25.6 g of bromohydrine (II) and 14.45 g of diethylamine in 70 ml of absolute ethanol is treated under reflux for 19 hours until disappearance of starting material has occurred (TCL). The ethanol is distilled off under vacuum and the residue is taken up in 250 ml of 6N HCl, under three-times extraction with 100 ml of chloroform; the organic extracts are washed twice with 100 ml of 6N HCl. The acid solutions are blended under cooling and stirring, then made alkaline with conc. NH$_4$OH until a highly-alkaline pH is obtained; the separated resin is extracted with chloroform and dried. By concentration, 9.65 g (39%) of a yellowish, non-crystallizing liquid are obtained.

IR Spectrum (film), cm$^{-1}$: 3420, 2970-2820, 1500, 1485, 1435, 1370, 1240, 1190, 1065, 1040, 935, 790.

RPM Spectrum (CDCl$_3$), ppm: 0.80-1.25 (2t±d, 9H; 2 CH$_2$—CH$_3$) and CH$_3$—CH), 2.3-2.7 (2 q, 4H, J=6.7

Hz; —CH$_2$—CH$_3$), 3.22 (d, 1H, J=5, 3 Hz; >CH—N<), 4.09 (m, 1H; —CHOH), 5.78 (s, 2H; —OCH$_2$—O—), 6.08 and 6.55 (s, 3H; Ar—).

Hydrochloride formation: the crude base is dissolved in 150 ml of dry ethyl ether and, under cooling and stirring, 4.5 ml of HCl (g) in 11N ethanol are added in dropwise fashion. The white precipitate is filtered off after a few hours and dried; 8.4 g (yield; 30%) are obtained, m.p. 181°–5° C. (d) and analysis C, H, N, Cl is correct.

IR Spectrum (BKr), cm$^{-1}$: 3300, 3060, 2990–2460, 1505, 1490, 1440, 1410, 1255, 1040, 930, 805, 790.

EXAMPLE 5 d,l-erythro-1-(3',4'-methylenedioxyphenyl)-1-piperidinepropane-2-ol (I, R$_1$R$_2$=—(CH$_2$)$_5$—)

As in the preceding Example, 25.0 g of bromohydrin and 16.45 g of piperidine are treated under reflux in 65 ml of ethanol for 16 hours. By an appropriate treatment, 17.6 g of solid base (yield: 69%) are isolated which following recrystallization in acetonitrile (25 ml) yields 10.15 g (40%) of white a solid, m.p. 72.3°–73.9° C. and elemental analysis is correct.

IR Spectrum (KBr), cm$^{-1}$: 3200, 3010, 2990–2700, 1495, 1480, 1430, 1240, 1135, 1035, 935, 875, 805, 790.

RPM Spectrum (CDCl$_3$), ppm: 0.97 (d, 3H, J=6.70 Hz; CH$_3$—), 1.48 (wide, 6H; —(CH$_2$)$_3$—), 2.40 (wide, 4H;

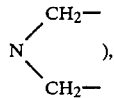

2.83 (wide, 1H; —OH), 2.98 (d, 1H, J=4.7 Hz; >CH—N<), 4.34 (q, 1H, J=6.0 Hz; —CHOH—), 5.96 (s, 2H; O—CH$_2$—O), and 6.75 and 6.87 (s, 2H and 1H; Ar—).

Hydrochloride formation: the recrystallized base is dissolved in 200 ml of anhydrous ethyl ether and, under cooling and stirring, 5.0 ml of HCl (g) in 11N ethanol are added. The hydrochloride separates with a quantitative yield as a white solid, m.p. 217°–9° C. and analysis C, H, N and Cl is correct.

IR Spectrum (KBr), cm$^{-1}$: 3280, 3230, 3000–2900, 2860–2600, 1480, 1440, 1370, 1250, 1085, 1030, 930, 860, 810.

EXAMPLE 6 d,l-erythro-1-(3',4'-methylenedioxyphenyl)-1-(4-hydroxypiperidine)-propane-2-ol (I, R$_1$,R$_2$=—(CH$_2$)$_2$CHOH(CH$_2$)$_2$—)

As in Example 2, 25.0 g of bromohydrin (II) and 21.7 g of 90% 4-hydroxypiperidine are treated under reflux in 150 ml of anhydrous toluene for 48 hours. By an appropriate treatment, 18.74 g (yield: 69%) of base are obtained as a viscous noncrystallizing liquid.

Hydrochloride formation: the base is dissolved in a mixture of 300 ml of methylene chloride and 700 ml of ethyl ether. Then 8.5 ml of HCl (g) in 11N ethanol are added under cooling and stirring. After a few hours, the mixture is filtered and dried, thus obtaining 18.32 g of solids which on recrystallization in ethanol and active carbon yields 8.02 g (20%) of a white solid, m.p. 205°–206.5° C. (d) and elemental analysis C, H, N and Cl is correct.

IR Spectrum (KBr), cm$^{-1}$: 3280, 3340, 3280, 3020, 2990, 2910, 2840–2600, 1440, 1370, 1250, 1035, 930, 920.

Neutralization of the hydrochloride with conc. NH$_4$OH, extraction with ethyl acetate and evaporation results in the isolation of the base in pure state, m.p. 75° C.

IR Spectrum (KBr), cm$^{-1}$: 3400 3005, 2960–2920, 2800, 2680, 1495, 1480, 1430, 1240, 1090, 1050, 1035, 930.

RPM Spectrum (CDCl$_3$), ppm: 1.00 (d, 3H, J=6.7 Hz; CH$_3$—), 1.4–2.9 (8H;

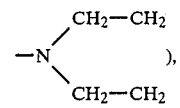

3.08 (d, 1H, J=5.3 Hz; >CH—N<), 3.72 (m, 1H;

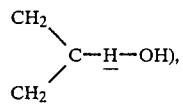

4.40 (q, 1H, J=6.0 Hz; CH$_3$—CHOH), 6.07 (s, 2H; O—CH$_2$—O), and 6.88 and 7.00 (s, 2H and 1H; Ar—).

EXAMPLE 7 d,l-erythro-1-(3',4'-methylenedioxyphenyl)-1-pyrrolidinopropane-2-ol (I, R$_1$R$_2$=—(CH$_2$)$_4$)

A mixture of 25.0 g of bromohydrin (II) and 13.73 g of pyrrolidine is treated under reflux in 65 ml of absolute ethanol for 19 hours, till disappearance of starting material. By treating this mixture as described in Example 4, a basic material is separated out, 21.9 g (yield: 91%) which solidifies with time. Recrystallization in out of diisopropyl ether (50 ml) yields 13.08 g (52%) of a white solid, m.p. 92°–93.2° C. and elemental analysis C, H, N is correct.

IR Spectrum (KBr), cm$^{-1}$: 3240, 3000, 2960, 2880, 2820, 2800, 1520, 1480, 1435, 1250, 1080, 1040, 940, 920, 805.

RPM Spectrum (CDCl$_3$), ppm: 0.88 (d, 3H, J=5.3 Hz; CH$_3$—), 1.52–2.07 (wide, 4H; —(CH$_2$)$_2$—), 2.20–2.80 (wide, 4H;

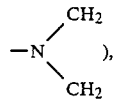

2.87 (d, 1H, J=2.8H (''); >CH—N<), 2.57 (s, 1H; —OH), 4.12 (m, 1H, —CHOH), 5.82 (s, 2H; O—CH$_2$—O), and 6.60 and 6.74 (s, 2H and 1H; Ar—).

Hydrochloride formation: 12.1 g of the recrystallized base are dissolved in 300 ml of ethyl ether and, under cooling and stirring, 6.4 ml of 11N HCl in ethanol are added; after standing over night at 0° C., the hydrochloride is filtered off and dried thus obtaining 13.2 g of the hydrochloride as a white solid, m.p. 203°–207° C. (d) and elemental analysis is correct.

IR Spectrum (KBr), cm$^{-1}$: 3280, 3010, 2990, 2930, 2880–2600, 1500, 1490, 1320, 1255, 1095, 1040, 920.

EXAMPLE 8 d,l-erythro-1-(3',4'-methylenedioxyphenyl)-1-homopiperidino-propane-2-ol (I, $R_1,R_2$=—$(CH_2)_6$—)

A mixture of 25.0 g of bromohydrin (II) and 19.5 g of homopiperidine are treated under reflux in 150 ml of toluene for 72 hours. The insolubilized homopiperidine hydrochloride (14.0 g dry) is filtered off after cooling and the toluene liquors are treated as in the preceding examples. 16.2 g of basic material are obtained which solidifies with time. Recrystallization in methanol-water (2:1), (125 ml), results in the isolation of 5.4 g (20.5%) of a white solid, m.p. 71°–73° C. and elemental analysis is correct.

IR Spectrum (KBr), cm$^{-1}$: 3580, 3450, 2970, 2920, 2850, 2810, 1500, 1490, 1435, 1240, 1070, 1240, 1070, 1035, 935, 820.

RPM Spectrum (CDCl$_3$), ppm: 1.03 (d, 3H, J=6.0 Hz; CH$_3$—), 1.5–2.0 (wide, 8H; —(CH$_2$)$_4$—), 2.5–3.1 (wide, 4H;

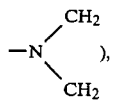

), 3.31 (d, 1H, J=5.3 Hz; >CH—N<), 4.26 (q, 1H, J=5.3 Hz; —CHOH—), 5.96 (s, 2H; O—CH$_2$—O), 6.6–7.0 (m, 3H; Ar—).

Hydrochloride formation: the recrystallized base is dissolved in 150 ml of dry ethyl ether and, under cooling and stirring, it subjected to a slow stream of dry HCl (g) until complete precipitation of the hydrochloride. After 3 hours in an ice bath the hydrochloride is filtered off and dried. 5.7 g of hydrochloride are obtained, m.p. 191°–4° C., and elemental analysis is correct.

IR Spectrum (KBr), cm$^{-1}$: 3440, 3280, 3010, 2980, 2930, 2880–2600, 1495, 1485, 1440, 1250, 1040, 920.

EXAMPLE 9 d,l-erythro-1-(3',4'-methylenedioxyphenyl)-1-benzylaminopropane-2-ol (I, $R_1$=H, $R_2$=—$CH_2$—Ph)

A mixture of 25.0 g of bromohydrin (II) and 20.7 g of benzylamine in 150 ml of toluene are mixed under reflux for 48 hours. The insolubilized benzylamine bromohydrate (14.9 g dry) formed is filtered off, cooled once and by properly treating, 6.5 g of base product (23.6%) are isolated (as a resinous, non-crystalline product).

Hydrochloride formation: the preceding base is dissolved in ethyl ether 100 ml anhydrous and under cooling 2 ml of HCl (g) solution in ethanol 11N are added following continuous cooling for 3 hours, the hydrochloride is filtered off and dried. 5.0 g of the hydrochloride are obtained which are recrystallized in isopropanol (50 ml) yielding 2.5 g of a white solid, m.p. 201°–5° C. (d) and elemental analysis correct.

IR Spectrum (KBr), cm$^{-1}$: 3360, 3020, 2990–2890, 2850–2800, 1500, 1485, 1435, 1245, 1035, 925, 810, 745, 690.

Neutralization of the hydrochloride with conc. NH$_4$OH and extraction with CHCl$_3$ results in the isolation of the pure base as a viscous, limpid liquid.

IR Spectrum (Film), cm$^{-1}$: 3350, 3030, 3020, 2960, 2880, 1495, 1480, 1435, 1240, 1095, 1035, 930, 810, 595.

RPM Spectrum (CDCl$_3$), ppm: 1.02 (d, 3H, J=6.7 Hz; CH$_3$—), 2.33 (wide, 2H; —OH and —NH—), 3.5–3.8 (m, 3H; —NH—CH$_2$— and —NH—CH<), 3.97 (m, 1H; —CHOH—), 5.97 (s, 2H; —O—CH$_2$—O—), 6.80 and 6.92 (s, 2H, Ar—) and 7.31 (s, 5H; Ar—).

EXAMPLE 10 d,l-erythro-1-(3',4'-methylenedioxyphenyl)-1-(N-methylbenzylamino)-propane-2-ol (I, $R_1$=CH$_3$, $R_2$=—CH$_2$—Ph)

A mixture of 25.0 g of bromohydrin (II) and 28.4 g of N-methylbenzylamine in 150 ml of toluene is treated under reflux for 72 hours. The insolubilized bromohydrate formed (17.3 g dry) is filtered and by properly treating, 4.5 g (17%) of a resinous, non-crystallined, base product are obtained; elemental analysis is correct.

IR Spectrum (KBr), cm$^{-1}$: 3440, 3030, 2980, 2900, 2800, 1500, 1485, 1440, 1365, 1245, 1035, 930, 810, 740.

RPM Spectrum (CDCl$_3$), ppm: 1.13 (d, 3H, J=6.0 Hz; CH$_3$—), 2.17 (s, >3H; N—CH$_3$), 3.22 (d, 1H, J=6.0 Hz; >CH—N<), 3.40 (s, 1H; —OH), 3.55 (s, 2H; >N—CH$_2$—), 4.40 (m, 1H; —CHOH), 5.99 (s, 2H; O—CH$_2$—O), 6.87 and 7.00 (s, 3H; Ar—) and 7.38 (s, 5H; Ar—).

Hydrochloride formation: the base is dissolved in 100 ml of dry ethyl ether and at a temperature of 0°–5° C. HCl(g) is slowly bubbled in. After 2 hours, the insolubilized yelowish solid which is formed is filtered and dried: 3.6 g, m.p. 90°–4° C. (d) and analysis is correct.

IR Spectrum (KBr), cm$^{-1}$: 3400, 3020, 2970, 2920, 2800, 1495, 1485, 1440, 1245, 1030, 920, 740 and 690.

EXAMPLE 11 d,l-erythro-1-(3',4'-methylenedioxyphenyl)-1-(N-methylcyclohexylamino)-propane-2-ol (I, $R_1$=CH$_3$, $R_2$=c—Hexyl)

A mixture of 25.0 g of bromohydrin (II) and 2.85 g of N-methylcyclohexylamine in 65 ml of ethanol are treated under reflux for 19 hours. Under treatment as in the preceding examples, 5.54 g of a resinous, non-crystalline base material are isolated.

IR Spectrum (film), cm$^{-1}$: 3400, 3010, 2980, 2940, 2860, 2800, 1500, 1490, 1440, 1245, 1100, 1040, 935, 810.

RPM Spectrum (CDCl$_3$), ppm: 0.90 (d, 3H, J=6.7 Hz; CH$_3$—), 1.0–1.95 (wide, 10H; —(CH$_2$)$_5$—), 2.26 (3H; >N—CH$_3$), 3.23 (m, 1H;

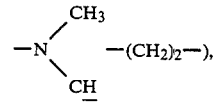

3.37 (d, 1H, J=4.7 Hz; Ar—C$\underline{H}$—N<), 4.33 (m, 1H; —C$\underline{H}$OH), 6.05 (s, 2H; —O—C$\overline{H}_2$—O—) and 6.73–7.07 (m, $\overline{3H}$; Ar—).

Hydrochloride formation: the base is dissolved in 100 ml of ethyl ether and under cooling at 0.°–5° C. dry HCl (g) is bubbled in until complete precipitation has taken place. After standing for a few hours at 0° C. it is filtered and dried: 4.85 g of precipitate are subjected to recrystallization in about 20 ml of isopropanol and yields 2.63 g of hydrochloride, a white solid, m.p. 194°–6° C. (d) and elemental analysis is correct.

IR Spectrum (KBr): 3250, 3020, 2940, 2860, 2680, 1495, 1485, 1440, 1245, 1040, 925, 810.

EXAMPLE 12 d,l-erythro-1-(3',4'-methylenedioxyphenyl)-1-cyclopropylaminopropane-2-ol (I, R$_1$=H, R$_2$=c—Pr)

A mixture of 25.0 g of bromohydrin (II) and 11.03 g of cyclopropylamine in 65 ml of ethanol are treated as in the preceding examples by isolating 8.4 g of base material (37%).

IR Spectrum (film), cm$^{-1}$: 3350, 3010, 2980, 2940–2780, 1500, 1485, 1440, 1240, 1040, 930, 805.

RPM Spectrum (CDCl$_3$), ppm: 0.33 and 0.42 (4H;

0.96 (d, 3H; J=6.0 Hz; CH$_3$—), 2.01

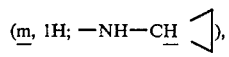

2.36 (wide, 2H; OH and NH), 3.55 (d, 1H, J=4.7 Hz; —C$\underline{H}$—NH—), 3.81 (m, 1H; C$\underline{H}$OH), 5.83 (s, 2H; O—C$\overline{H}_2$—O) and 66.5 and 6.73 (s, $\overline{3H}$; Ar—).

Hydrochloride formation: the base is dissolved in 150 ml of ethyl ether and under cooling at 0.°–5° C. dry HCl(g) is bubbled in. After standing a few hours under stirring at 0° C., it is filtered and dried: 8.07 g white solid are recovered having a, m.p. 90° C. (d) and analysis is correct.

IR Spectrum (KBr), cm$^{-1}$: 3380, 2980, 2840–2600, 1495, 1485, 1440, 1245, 1030.

EXAMPLE 13 d,l-erythro-1-(3',4'-methylenedioxyphenyl)-1-cyclohexylaminopropane-2-ol

A mixture of 61.65 g of bromohydrin (II) and 47.20 g of cyclohexylamine in 350 ml of toluene is treated under reflux for 48 hours. Under treatment as described in the preceding examples, 19.2 g of a resinous, non-crystallized, base material (29%) are isolated.

Hydrochloride formation: the above base is dissolved in ethyl ether and under cooling dry HCl(g) is slowly bubbled in. After a few hours at 0° C., the hydrochloride salt is filtered and dried: 19.7 g of yellowish solid are recovered which on recrystallization from acetonitrile (80 ml) yields 7.42 g of white hydrochloride, m.p. 210°–3° C. and elemental analysis is correct.

IR Spectrum (KBr), cm$^{-1}$: 3390, 2970, 2930, 2850–2600, 1500, 1485, 1450, 1440, 1250, 1230, 1100, 1030, 930, 815.

By neutralization of the hydrochloride and recrystallization there it isolated the base as a white solid, m.p. 95.5°–97° C. and elemental analysis correct.

IR Spectrum (KBr), cm$^{-1}$: 3160, 3000, 2970, 2920, 2860, 2840, 2760, 1500, 1480, 1435, 1370, 1230, 1100, 1040, 940, 915, 850, 800.

RPM Spectrum (CDCl$_3$), ppm: 0.99 (d, 3H, J=6.0 Hz; CH$_3$—), 1.1–2.5 (wide, 13H; cyclohexanic and and C$\underline{H}$—N$\underline{H}$—), 3.6–4.1 (m, 2H; —C$\underline{H}$OH—), 5.97 (s, 2H; —O—C$\overline{H}_2$—O—) and 6.84 and 6.$\overline{78}$ (s, 3H; Ar).

We claim:

1. A compound selected from the group consisting of 1-position amino derivatives of 1-(3',4'-methylenedioxyphenyl)-propane-2-ol having the formula

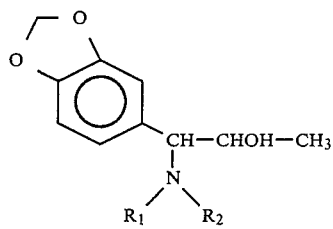

wherein R$_1$ and R$_2$ are each independently selected from the group consisting of hydrogen, alkyl having a maximum of 2 carbon atoms, cycloalkyl having 3 to 6 carbon atoms and benzyl, provided that R$_1$ and R$_2$ are not both hydrogen, cycloalkyl or benzyl and where R$_1$ and R$_2$ taken together with the nitrogen atom to which they are attached can form a ring having 5 to 7 bonds, which ring may contain another heteroatom selected from the group of oxygen and nitrogen and wherein said ring can be substituted with a member selected from the group consisting of benzyl and hydroxyl; and the non-toxic acid addition salts thereof.

2. A compound according to claim 1 designated d,l-erythro-1-(3',4'-methylenedioxyphenyl)-1-morpholine-propane-2-ol.

3. A compound according to claim 1 designated d,l-erythro-1-(3',4'-methylenedioxyphenyl)-1-(4-benzyl-1-piperazinyl)-propane-2-ol.

4. A compound according to claim 1 designated d,l-erythro-1-(3',4'-methylenedioxyphenyl)-1-diethylaminopropane-2-ol.

5. A compound according to claim 1 designated d,l-erythro-1-(3',4'-methylenedioxyphenyl)-1-piperidinopropane-2-ol.

6. A compound according to claim 1 designated d,l-erythro-1-(3',4'-methylenedioxyphenyl)-1-(4-hydroxyl-piperidino)-propane-2-ol.

7. A compound according to claim 1 designated d,l-erythro-1-(3',4'-methylenedioxyphenyl)-1-pyrrolidinopropane-2-ol.

8. A compound according to claim 1 designated d,l-erythro-1-(3',4'-methylenedioxyphenyl)-1-homopiperidino)propane-2-ol.

9. A compound according to claim 1 designated d,l-erythro-1-(3',4'-methylenedioxyphenyl)-1-benzylaminopropane-2-ol.

10. A compound according to claim 1 designated d,l-erythro-1-(3',4'-methylenedioxyphenyl)-1-(N-Methyl-benzylamino)-propane-2-ol.

11. A compound according to claim 1 designated d,l-erythro-1-(3′,4′-methylenedioxyphenyl)-1-(N-Methylcyclohexylamino)-propane-2-ol.

12. A compound according to claim 1 designated d,l-erythro-1-(3′,4′-methylenedioxyphenyl)-1-cyclopropylaminopropane-2-ol.

13. A compound according to claim 1 designated d,l-erythro-1-(3′,4′-methylenedioxyphenyl)-1-cyclohexylaminopropane-2-ol.

14. A therapeutic composition having analgesic activity comprising an analgesically effective amount of a compound according to claim 1 as active ingredient in admixture with a pharmaceutically acceptable carrier.

15. A therapeutic composition according to claim 14 in dosage unit form.

16. A therapeutic composition according to claim 15 containing 500–5000 mg of active ingredient per dosage unit.

17. Method of inducing analgesia in a mammal comprising administering an analgesically effective amount of a compound according to claim 1.

18. Method according to claim 17 wherein there is administered from 500–5000 mg of compound per day.

* * * * *